United States Patent [19]
Heidler et al.

[11] Patent Number: 5,976,866
[45] Date of Patent: Nov. 2, 1999

[54] SCREEN FOR INHIBITORS OF FUNGAL IPC SYNTHASE

[75] Inventors: Steven Alan Heidler, Fishers; Jeffrey Alan Radding, Carmel; Debra Ann Young, Danville, all of Ind.

[73] Assignee: Eli Lilly and Company, Indianapolis, Ind.

[21] Appl. No.: 08/833,814

[22] Filed: Apr. 9, 1997

[51] Int. Cl.$^6$ ............................. C12N 1/16; C12N 15/00
[52] U.S. Cl. ................. 435/254.21; 435/254.11; 435/172.1
[58] Field of Search ............... 435/29, 471, 477, 435/254.1, 254.11, 254.21, 254.3, 172.1

[56] References Cited

FOREIGN PATENT DOCUMENTS

| 0 644 242 A2 | 3/1995 | European Pat. Off. . |
| 0 692 534 A2 | 1/1996 | European Pat. Off. . |

OTHER PUBLICATIONS

Takashi Hashida–Okada, et al. "AUR1, a novel gene conferring aureobasidin resistance on *Saccharomyces cerevisiae:* a study of defective morphologies in Aur1p–depleted cells." *Mol. Gen. Genet.* 215:236–244 (1996).

M. Marek Nagiec, et al. "Sphingolipid Synthesis as a Target for Antifungal Drugs." *The Journal of Biological Chemistry* 272(15):9809–9817 (Arpr. 11, 1997).

Hashida–Okado et al. "Cloning and Characterization of a gene confering resistance to the antifungal antibiotic aureobasidin A (R106–1) in yeast" Biochemical Pharmacology May 1, 1995; 11: A1371.

Heidler SA, et al. "The AUR1 gene in *Saccharomyces cerevisiae* encodes dominant resistance to the antifungal agent aureobasidin A (LY295337)" Antimicrob Agents Chemother. Dec. 1, 1995; 39(12): 2765–2769.

Schneider et al. "Vectors for expression of cloned genes in yeast: Regulation, overproduction, and underproduction" Method in Enzymology (Jan. 14, 1991) vol. 194, pp. 373–388.

Baudin A, et al. "A simple and efficient method for direct gene deletion in *Saccharomyces cerevisiae*" Nucleic Acids Res. Jul. 11, 1993; 21(14): 3329–3330.

Sikorski RS, et al. "A system of shuttle vectors and yeast host strains for designed effieicient manipulation of DNA in *Saccharomyces cerevisiae*" Genetics. May 1, 1989; 122(1): 19–27.

*Primary Examiner*—Ponnathapura Achutamurthy
*Assistant Examiner*—Bradley S. Mayhew
*Attorney, Agent, or Firm*—Raymond S. Parker III; Thomas D. Webster

[57] ABSTRACT

This invention provides novel fungal strains altered in IPC synthase production, and a method for screening for inhibitors of fungal IPC synthase using whole cells.

1 Claim, 2 Drawing Sheets

SCREEN FOR INHIBITORS OF FUNGAL IPC SYNTHASE

BACKGROUND OF THE INVENTION

This invention relates to the analytical arts and to recombinant DNA technology. In particular the invention pertains to the construction and purification of novel strains of yeast and other fungi that are useful in whole-cell screens for inhibitors of inositolphosphoryl ceramide synthase (IPC Synthase).

The incidence of life-threatening fungal infections is increasing at an alarming rate. With the exception of Staphylococci infections, the fungus C. albicans represents the fastest growing area of concern in hospital acquired infections. About 90% of nosocomial fungal infections are caused by species of Candida with the remaining 10% being attributable to Aspergillus, Cryptococcus, and Pneumocystis. While effective antifungal compounds have been developed for Candida there is growing concern that the rise in fungal infections may portend a trend toward escalating resistance and virulence in the future. This is problematic because anti-Candida compounds rarely possess clinically significant activity against other fungal species.

Inositolphosphoryl ceramides are sphingolipids found in a number of fungi including but not limited to S. cerevisiae, S. pombe, C. albicans, A. fumigatus, and H. capsulatum. A step of sphingolipid biosynthesis that is unique to fungi and plants is catalyzed by the enzyme IPC synthase. The IPC synthase step, which covalently links inositol phosphate and ceramide, is essential for viability in S. cerevisiae. Although some elements of sphingolipid biosynthesis in fungi are shared with mammalian systems, the pathways diverge after formation of ceramide. Thus, the formation of inositolphosphoryl ceramide is unique to fungi and plants, making IPC synthase a good molecular target for antifungal chemotherapy.

While IPC synthase presents a rational target for antifungal therapy, presently there are no clinically useful compounds that act at this step. Thus, there is a need for new compounds that inhibit IPC synthase.

BRIEF SUMMARY OF THE INVENTION

The present invention relates to fungal IPC synthase and to whole-cell screens for inhibitors thereof.

In one embodiment the invention relates to novel fungal strains in which IPC synthase is produced at levels that differ from wild-type cells.

In another embodiment, the invention relates to novel fungal strains in which a gene that encodes IPC synthase or subunit thereof is operably-linked to a heterologous promoter such that IPC synthase is produced at levels that differ from wild-type cells.

In another embodiment the present invention pertains to high throughput screens for inhibitors of fungal IPC synthase.

DEFINITIONS

Figure 1:
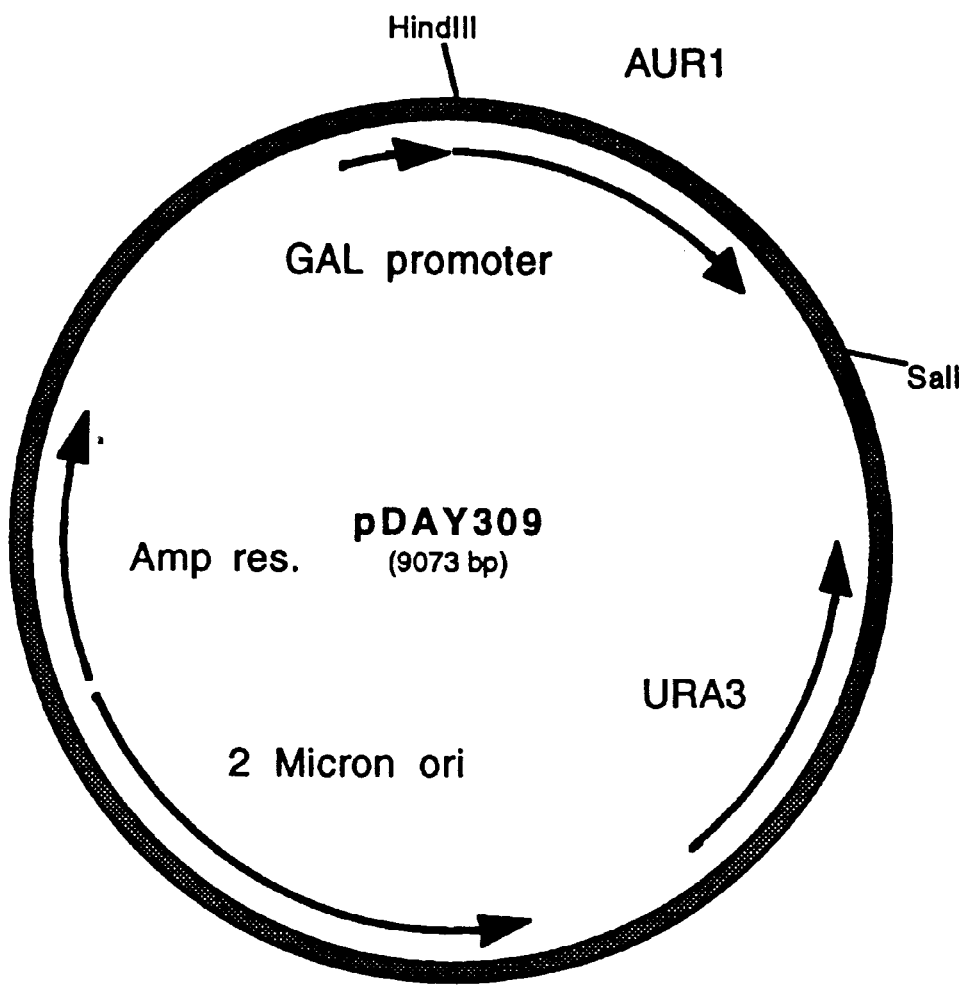
FIG. 1. Plasmid pDAY307 is a 2μ yeast vector that carries a modified aur1$^+$ gene. pDAY307 was constructed in vector pYX212 (available from Novagen, 597 Science Dr., Madison, Wis. 53711), which is a multi-copy vector that carries the URA3 gene and cloning sites for expressing a gene from a TPI promoter.

"aur1$^+$" refers to a gene of yeast that when mutated confers resistance to aureobasidin A. Aureobasidins are antifungal cyclic peptides isolated from Aureobasidium pullulans R106-1 (Takesako et al. J. Antibiot. 44, 919–924, 1991). aur1$^+$ encodes IPC synthase or a subunit of the IPC synthase enzyme. Aureobasidin A (R106-1) inhibits IPC synthase activity in vitro.

"Δaur1$^+$" refers to a deletion mutation in the aur1$^+$ locus.

"Hypersensitive" refers to a phenotype in which cells are more sensitive to antifungal compounds than are wild-type cells of similar or identical genetic background. As used herein, "hypersensitive" means that cells are at least 20-fold more sensitive than wild-type, when grown under identical conditions.

"TPI" refers to the yeast triose phosphate isomerase gene. The TPI promoter is used as a strong constitutive promoter for expression of heterologous genes in yeast (R. Schiestl and R. Gietz, Curr. Genet. 16, 339–46, 1989).

"GAL" refers to a structural gene associated with galactose metabolism in yeast. The GAL1 gene, for example, encodes the enzyme galactokinase. The GAL1 promoter, when operably-linked to a heterologous gene, is useful for providing galactose inducibility and glucose repressibility (M. Johnston and R. W. Davis, Mol. Cell. Biol. 4, 1440–48, 1984).

"nmt" (no message in thiamine) refers to thiamine responsive yeast promoters of various strengths.

"YEPD" refers to a rich medium for growing yeast cells. YEPD comprises 1% yeast extract, 2% Bacto-peptone, and 2% glucose.

"SC-URA" refers to a synthetic complete medium that lacks uracil. It comprises, per liter, 1.7 g yeast nitrogen base (without amino acids and ammonium sulfate), 5.0 g ammonium sulfate, 0.8 g CSM-URA (available from BIO 101, 1070 Joshua Way, Vista, Calif. 92083), and 20 g of any suitable carbon source (e.g. glucose, raffinose, sorbitol, or galactose).

The term "deletion mutation" as used herein includes mutations that remove some or all of the DNA that comprises a structural gene or regulatory region for such gene. Also contemplated by the term are mutations that remove DNA from a structural gene and/or its regulatory region and insert therefore a heterologous fragment of DNA that may encode another gene.

"Knockout cassette" means a fragment of native chromosomal DNA having cloned therein a foreign piece of DNA that may provide a selectable marker.

"Recombinant DNA cloning vector" as used herein refers to any autonomously replicating or integrating agent, including, but not limited to, plasmids and phages, comprising a DNA molecule onto which one or more additional DNA segments can or have been added.

The term "expression vector" as used herein refers to any recombinant DNA cloning vector, for example a plasmid or phage, in which a promoter and other regulatory elements are present to enable transcription of the inserted DNA.

The term "vector" as used herein refers to a nucleic acid compound used for introducing exogenous DNA into host cells. A vector comprises a nucleotide sequence which may encode one or more protein molecules. Plasmids, cosmids, viruses, and bacteriophages, in the natural state or which have undergone recombinant engineering, are examples of commonly used vectors.

The term "whole-cell screen" refers to the use of whole fungal cells, for example yeast cells, in screens for compounds that inhibit or otherwise alter the growth of said cells on a defined medium. As used herein the term relates to screens for inhibitors of fungal IPC synthase using yeast or other fungi that produce altered levels of IPC synthase or a subunit of the IPC synthase enzyme.

DETAILED DESCRIPTION OF THE INVENTION

In yeast and other fungi, such as *C. albicans, A. fumigatus, C. neoformans, C. krusei, C. parapsilosis, C. tropicalis,* and *C. glabrata,* for example, IPC synthase catalyzes a step in the synthesis of inositolphosphoryl ceramide from ceramide and phosphatidylinositol (G. Becker and R. Lester, Biosynthesis of phosphoinositol-containing sphingolipid from phosphatidylinositol by a membrane preparation from *Saccharomyces cervisiae. J. Bacteriol.* 142, 747–754, 1980). Sphingolipids are necessary for growth and viability of the yeast *S. cerevisiae.* Since IPC synthase is unique to fungi and plants it is a good target for antifungal therapy.

This invention relates to the use of fungal cells in whole-cell screens for inhibitors of IPC synthase. The methods contemplated herein relate to cells that have been modified to express more or less IPC synthase activity than wild-type cells. Cells that are suitable for this purpose could arise, for example, through alterations in the expression of the gene that encodes IPC synthase or subunit thereof, or through alterations in the IPC synthase enzyme itself. Cells having these characteristics can be generated through chemical or UV mutagenesis by well known means, or by recombinant DNA techniques in which, for example, an IPC synthase gene is operably-linked to a heterologous promoter. Transcription from a heterologous promoter is expected to alter expression of an operably-linked gene. The methods contemplated herein are preferably carried out by recombinant DNA techniques.

The genes that encode IPC synthase or subunit thereof from *S. cerevisiae, S. pombe,* and *C. albicans* have been described (EP 0 644 262 A2). Methods for introducing mutations into cloned DNA and for linking genes to heterologous promoters are well known to the skilled artisan (See generally, Maniatis et al. *Molecular Cloning,* Cold Spring Harbor, 1982). A number of suitable heterologous promoters are contemplated including the TPI promoter, the GAL promoters, and nmt promoters, for example. The skilled artisan also recognizes that methods and techniques other than those exemplified herein could be employed to accomplish the same objective and these are intended to be within the scope of the present invention.

The methods disclosed herein relate to the use of whole cells that express altered levels of IPC sythase. For example, cells that express less than wild-type levels of IPC synthase may become more sensitive to inhibitors of IPC synthase. In a preferred embodiment, the methods disclosed herein use cells that are hypersensitive to IPC synthase inhibitors such as R106-1. Hypersensitivity may be achieved, for example, by introducing into fungal cells an expression vector that carries the gene encoding IPC synthase or subunit thereof, such that expression of said gene can be regulated, or maintained at levels that differ from wild-type. The skilled artisan will recognize a number of suitable expression vectors that incorporate a variety of ARS, 2m, or CEN replication and segregation elements for expression in *S. cerevisiae* (See e.g. R. Sikorski & P. Hieter, *Genetics,* 122, 19–26, 1989).

The present invention contemplates application to any suitable fungal cell. Examples of suitable cells include *C. albicans, A. fumigatus, C. neoformans, C. krusei, C. parapsilosis, C. tropicalis, C. glabrata, S. cerevisiae,* and *S. pombe.* Recombinant DNA techniques such as transformation and the like are available for these cells (See e.g. J. Pla et.al. *Yeast,* 12, 1677–1702, 1996; S. Moreno et.al. *Meth. Enzymol.* 194, 795–823, 1991). Without intending to limit the scope of the invention, the method will be described in detail with reference to *S. cerevisiae.*

In *S. cerevisiae,* the aur1$^+$ gene encodes IPC synthase or a subunit of IPC synthase. The aur1$^+$ recombinant strains described in this invention were created in an Δaur1$^+$ genetic background. Since the Δaur1$^+$ genotype is lethal in haploid cells on all media tested, it was necessary to begin with a diploid strain in order to create an Δaur1$^+$ deletion at one of the chromosomal alleles. Strain YPH501 was used for this purpose (MATa/a ura3-52 lys2-801 ade2-101 trp1-Δ63 his3-D200 leu2-D1; R. Sikorski & P. Hieter, *Genetics,* 122, 19–26, 1989).

An Δaur1$^+$/aur1$^+$ heterozygous diploid was produced by transforming YPH501 with a knockout cassette comprising three elements: at the two ends of the cassette are sequences that flank aur1$^+$ on the yeast chromosome; in the center of the cassette is any suitable marker, for example the TRP1 gene. Other genetic marker genes, well known to the skilled artisan, could also be used for this purpose, for example, HIS3, URA3, and LEU2. Using the knockout cassette, Trp$^+$ transformants of YPH501 were selected and tested by Southern hybridization to identify isolates that had undergone a recombination event at the aur1$^+$ locus.

A suitable heterozygous diploid having the desired aur1$^+$::TRP1/aur1$^+$ genotype was identified by sporulation and tetrad analysis, revealing 2 viable spores and 2 nonviable spores. This isolate was transformed with a 2μ yeast vector (either pDAY307 or pDAY309) that carries a modified aur1$^+$ gene. The pDAY vectors were constructed in Novagen vectors pYX212 and pYX213, which are multi-copy vectors carrying the URA3 gene and cloning sites that enable expression from TPI(pDAY307) or GAL1(pDAY309) promoters (Novagen, Inc. 597 Science Drive, Madison, Wis. 53711). The protein that is produced by the aur1$^+$ gene on the pDAY vectors is modified by the addition of 14 amino acids at the N terminal side of the initiator Methionine. Additionally, the aur1$^+$ gene on the pDAY vectors is operably-linked to the TPI promoter (pDAY307) or to the GAL1 promoter (pDAY309). The aur1$^+$ gene can be isolated most conveniently by the polymerase chain reaction (PCR) using suitable oligonucleotide primers. The nucleotide sequence for aur1$^+$ is available from The Stanford Genome World Wide Web site (URL:http://genome-www.stanford.edu/Saccharomyces/); the sequence of an R106-1 resistant allele is also available, See e.g. Heidler and Radding, *Antimicrob. Agents Chemother.* 39, 2765–69, (1995). The PDAY vectors enable regulated expression of a functional IPC synthase as evidenced by rescue of aur1$^+$::TRP1 cells from nonviability. Suitable strains were isolated by sporulation, dissection, and identification of aur1$^+$::TRP1pDAY307 or pDAY309-containing Ura$^+$ segregants.

The *S. cerevisiae* strains described in this invention are listed in Table 1 along with their relevant genotypes.

TABLE 1

| aur1+-Modified S. cerevisiae | Strains | Genotype |
| --- | --- | --- |
| YPH499Daur1+ (pDAY307) | Strain A | MATa ura3-52 lys2-801 ade2-101 trpl-Δ63 his3-D200 leu2-D1 aur1+::TRP1 pDAY307 |
| YPH499Daur1+ (pDAY309) | Strain B | MATa ura3-52 lys2-801 ade2-101 trpl-D63 his3-D200 leu2-D1 aur1+::TRP1 pDAY309 |

The yeast strains relating to the present invention afford regulatable expression of the aur1+ gene in S. cerevisiae. Strain A, for example, provides expression of a vector-borne aur1+ gene operably-linked to the TPI yeast promoter. This construct results in constitutive expression of IPC synthase.

Strain B, on the other hand, provides a vector-borne aur1+ gene whose expression is regulatable. The plasmid-borne aur1+ gene in Strain B is operably-linked to the GAL1 yeast promoter, which imparts inducibility when cells are grown on galactose; moreover, the GAL1 promoter imparts glucose repressibility in vivo leading to lowered expression of IPC synthase.

High-Throughput Screen for IPC Synthase Inhibitors Using aur1+—Altered Fungal Strains The strains contemplated by the present invention are useful in whole-cell screens for compounds that inhibit fungal IPC synthase. In one embodiment, test compounds are assayed for their affect on the rate of growth or viability of suitable cells. In a preferred embodiment of this method wild-type cells are compared against cells that manifest altered IPC synthase activity, via lowered expression of a gene encoding IPC synthase or subunit thereof.

For example, S. cerevisiae strains A and B (Table 1) are equally affected by antifungal compounds that do not target IPC synthase, such as amphotericin B, nystatin, echinocandin analog, cycloheximide, fluconazole, and ketoconazole (See Table 3).

In contrast, strains A and B differ markedly in their sensitivity to R106-1, a known inhibitor of IPC synthase. When strain A which provides expression of aur1+ from a TPI promoter) is exposed to R106-1, cells exhibit wild-type sensitivity on all media tested (see Table 2). On the other hand, strain B (aur1+ expression linked to the GAL1 promoter) exhibits hypersensitivity to R106-1 when cells are grown in a medium containing glucose (Table 2). Similar results were obtained using raffinose as the carbon source. Thus, strain B is at least 30-fold more sensitive than wild-type cells to R106-1, a compound known to inhibit IPC synthase.

This invention further contemplates the use of whole cells in high throughput screens of natural products, synthetic compounds, and compounds derived from combinatorial libraries to identify inhibitors of IPC synthase. For this purpose, a comparison is made between, for example, wild-type cells and cells in which IPC synthase gene expression is altered, preferably so that said alteration results in hypersensitivity to inhibitors of IPC synthase, such as R106-1. A screening system of this format would comprise the steps of:

a) cultivating suitable fungal cells on an appropriate liquid or solid medium;
b) exposing said cells to a test compound;
c) monitoring growth inhibition by any suitable means; and
d) comparing the inhibition of growth of wild-type cells with cells in which IPC synthase expression is modified.

In a preferred embodiment the cells are derived from strains A and B. This screening system may be adapted to automated procedures such as a PANDEX® system (Baxter-Dade Diagnostics), allowing for efficient high-volume screening of potential inhibitors.

The following examples more fully describe the present invention. Those skilled in the art will recognize that the particular reagents, equipment, and procedures described are merely illustrative and are not intended to limit the present invention in any manner.

EXAMPLE 1

Construction of an S. cerevisiae Strain Exhibiting Altered IPC Synthase Expression A deletion of the aur1+ locus of S. cerevisiae strain YPH501 was constructed as follows. First, a knockout cassette was constructed in order to replace the wild-type aur1+ chromosomal locus with the TRP1 gene. Using oligonucleotide primers, designated SEQ ID NO.1 and SEQ ID NO.2, a 909 base pair fragment of chromosomal DNA flanking the 3' end of aur1+ was PCR-amplified from yeast genomic DNA. Next, a 1086 base pair fragment was amplified from yeast chromosomal DNA flanking the 5' end of the aur1+ locus using primers designated SEQ ID NO.3 and SEQ ID NO.4. The PCR-amplified genomic fragments were ligated to a TRP1 gene (St. John et al. J. Mol. Biol. 152, 317–34, 1981) to form the knockout cassette used in the next step to delete the aur1+ locus.

The TRP1 knockout cassette was transformed into diploid strain YPH501. This strain carries a deletion mutation at the chromosomal TRP1 locus. Trp+ transformants were selected by plating cells onto synthetic complete medium, or minimal medium plus supplements lacking tryptophan. A transformant having the desired gene transplacement at the aur1+ locus was identified by sporulation and tetrad analysis. This analysis identified a suitable heterozygote as producing 2 viable spores and 2 non-viable spores. The relevent genotype of this heterozygote is aur1+::TRP1/aur1+.

Figure 2:
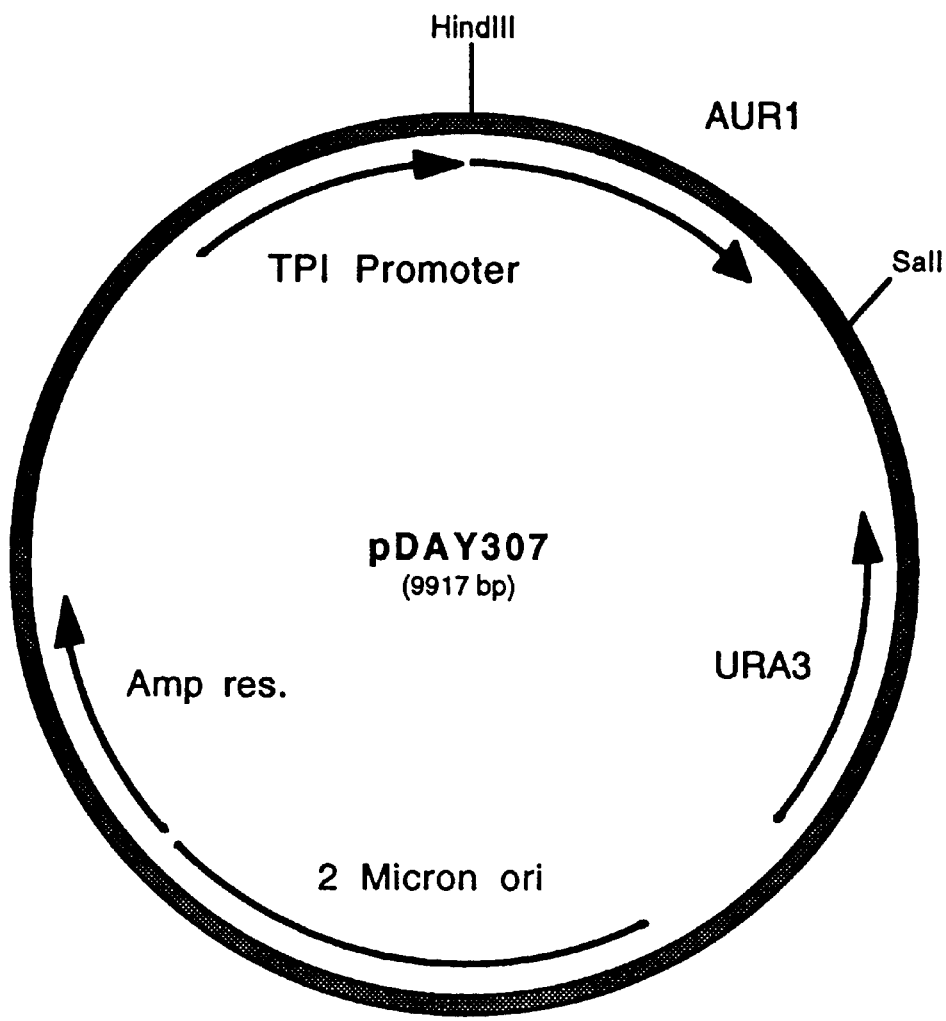
FIG. 2. Plasmid pDAY309 is a 2μ yeast vector that carries a modified aur1$^+$ gene. pDAY309 was constructed in Novagen vector pYX213, which is a multi-copy vector that carries the URA3 gene and provides cloning sites for expressing heterologous genes from a GAL1 promoter.

In order to isolate a haploid strain carrying the aur1+::TRP1 deletion allele, the aforementioned aur1+::TRP1/aur1+ heterozygote was transformed with an expression plasmid that carries the aur1+ gene in operable linkage with a TPI (pDAY307) or GAL1 (pDAY309) promoter (See FIGS. 1 and 2). Transformants were sporulated and two isolates having the correct phenotype (viz. Trp+ Ura+) were chosen for further study (designated Strain A (pDAY307) and Strain B (pDAY309) (See Table 1). Hypersensitivity in Strain B was conferred by the plamid-borne sequence under the control of the specified promoter. This was confirmed by transformation of Strain B with a second plasmid bearing a wild-type aur1+ sequence under the control of its own promoter. This transformant regained wild-type sensitivity upon loss of the pDAY309 plasmid.

EXAMPLE 2

Construction of a Strain of S. pombe Exhibiting Altered IPC Synthase Expression

A strain of S. pombe exhibiting underexpression of aur1+ is constructed in a manner analagous to Example 1. A gene replacement cassette is constructed as follows. Using PCR amplification, S. pombe chromosomal sequences are amplified from the 5' end (primers designated herein as SEQ ID NO 5 and SEQ ID NO 6), and 3'end (primers designated herein as SEQ ID NO 7 and SEQ ID NO 8) of the aur1+ locus. The amplified fragments are ligated onto the ends of a selectable marker, for example, the LEU2 gene using any suitable cloning linkers. The resulting gene disruption cassette may be cloned into any suitable integration vector (i.e. one lacking a pombe origin of DNA replication), for example the pUC, pBR, or Bluescript E. coli plasmids.

In order to create an aur1/aur1::LEU2 heterozygote, the LEU2 disruption cassette described in preceding paragraph is tranformed into a diploid strain having the following genotype: h−/h+ ura4-D18/ura4-D18 leu1-32/leu1-32 ade6-M210/ade6-M216. These diploid cells are white in color owing to cross-complementation by the ade6 alleles. Transformants are selected following the lithium acetate method, on minimal medium lacking leucine. (See Okazaki et al. Nuc. Acid Res. 18, 6485–89 (1990); Moreno et al. Meth. Enzym. 194, 795–823 (1991).

An expression vector that carries the wild-type aur1+ gene minus the gene's native promoter is cloned behind an nmt promoter, as follows. A 1383 base pair fragment of pombe genomic DNA carrying the aur1+ gene is amplified using the primers designated herein as SEQ ID NO 9 and SEQ ID NO 10. These primers carry BamH1 and Xho1 cloning sites, which when digested with said restriction enzymes, are suitable for cloning into a REP "X" vector. The REP X vector carries the URA4 gene, an nmt promoter, and a polylinker cloning site that lacks an ATG codon. (See e.g. Basi et al. Gene 123, 131–36 (1993); Forsburg, Nuc. Acid Res. 21, 2955–56 (1993); Maundrell, J. Biol. Chem. 265, 10857–864 (1990).

The aur1+ expression plasmid described above is transformed into the aur1/aur1::LEU2 heterozygote and transformants are selected on minimal medium lacking uracil, leucine, and thiamine. Transformants selected thusly are induced to sporulate by continued incubation. Haploid colonies are screened for by identifying "red" colonies (ade6 mutation leads to red color; segregation of complementing ade6 alleles in the diploid produces red haploid colonies). The haploid isolates are leu+ ura+ and express the aur1 gene product solely from the plasmid borne nmt promoter.

By growing the haploid constructs in medium that contains increasing amounts of thiamine one can identify a level of thiamine that represses expression of aur1+ to the lowest levels possible while retaining viability. These cells are expected to be hypersensitive to IPC synthase inhibitors, such as R106-1, and useful for the whole-cell screens described herein.

EXAMPLE 3

Differential Sensitivity of Strains A and B to R106-1

Overnight cultures of Strain A and Strain B were grown in YEPD. An aliquot of each overnight culture was diluted into fresh medium. Then about $10^4$ cells in 100 ul of medium were deposited into each well of a 96-well microtiter plate containing about 100 ml per well of medium plus decreasing amounts of R106-1, starting from 2.5 ug/ml and diminishing by successive 2-fold dilutions (R106-1 is available from Panvera Corp. 545 Science Drive, Madison, Wis. 53711). Innoculated plates were placed in a 30° C. incubator and checked for cell growth at 24 hours and 48 hours. Cells were resuspended after 48 hours and allowed to settle for at least one hour, when the cell density was determined at 590 nm using a microtiter plate reader.

The results of this experiment are summarized in Table 2. Strain B is from 30-fold to 100-fold more sensitive to R106-1 than either wild-type cells or cells from Strain A. Similar results were obtained using SC-URA (2% glucose) medium (Table 2), and when the cells were grown in medium containing 2% raffinose rather than 2% glucose (data not shown).

TABLE 2

Sensitivity of Strains A and B to R106-1
Minimum Inhibitory Concentration, ug/ml

| Strain | SC-URA Glucose | YEP Glucose |
|---|---|---|
| YPH499 [a] | 0.625 | 0.04 |
| Strain A | 0.625 | 0.04 |
| Strain B | 0.015 | 0.0006 |

[a] wild-type strain transformed with YEp352 (a vector that carries URA3 gene but not aur1+; Hill et al. Yeast, 2, 163–67, 1986).

EXAMPLE 4

Whole-Cell Screen of Yeast Strains using Non-IPC Synthase Inhibitors

Strains A and B, and wild-type strain YPH499 (transformed with YEp352) were tested for sensitivity to a variety of known antifungal compounds. Cells were grown in YEPD or SC-URA (2% glucose) liquid culture and dispensed into the wells of a 96-well microtiter dish containing decreasing amounts of antifungal compounds, as in Example 2.

The results of this experiment demonstrate that strains A and B behave similarly to wild-type cells when exposed to antifungal compounds that do not target IPC synthase (See Table 3).

TABLE 3

Sensitivity to Antifungal Compounds[a]
Minimum Inhibitory Concentration, mg/ml

| Compound | YPH499[b] | Strain A | Strain B |
|---|---|---|---|
| Amphotericin B | 2.5 | 2.5 | 2.5 |
| Nystatin | 20 | 20 | 20 |
| ECB analog[c] | 1.2 | 1.2 | 1.2 |
| Cycloheximide | 0.3 | 0.3 | 0.6 |
| Fluconazole | >80 | >80 | >80 |
| Itraconazole | 1.2 | 1.2 | 1.2 |

[a] Cells were grown in SC-URA (2% glucose)
[b] YPH499 is transformed by YEp352.
[c] Echinocandin analog

We claim:

1. A recombinantly modified *Saccharomyces cerevisiae* strain YPH499 comprising a deletion mutation at the aur1$^+$ chromosomal locus and comprising a vector-borne aur1$^+$ gene that is operably linked to a GAL promoter, wherein said recombinantly modified *Saccharomyces cerevisiae* strain YPH499 is viable on a medium that is devoid of galactose and that comprises glucose.

* * * * *

SEQUENCE LISTING (1) GENERAL INFORMATION:

(iii) NUMBER OF SEQUENCES: 10

(2) INFORMATION FOR SEQ ID NO:1:

(i) SEQUENCE CHARACTERISTICS:
         (A) LENGTH: 34 base pairs
         (B) TYPE: nucleic acid
         (C) STRANDEDNESS: single
         (D) TOPOLOGY: linear (ii) MOLECULE TYPE: other nucleic acid
         (A) DESCRIPTION: /desc = "oligonucleotide"

(iii) HYPOTHETICAL: NO (iv) ANTI-SENSE: NO (xi) SEQUENCE DESCRIPTION: SEQ ID NO:1:

GCAATTACGG ATCCGGTTGG TCTTATGTAG ATAC                                          34

(2) INFORMATION FOR SEQ ID NO:2:

(i) SEQUENCE CHARACTERISTICS:
         (A) LENGTH: 37 base pairs
         (B) TYPE: nucleic acid
         (C) STRANDEDNESS: single
         (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:2:

GAATACGCAT AACTCGAGAG GATGATTTCT GATTAGG                                       37

(2) INFORMATION FOR SEQ ID NO:3:

(i) SEQUENCE CHARACTERISTICS:
         (A) LENGTH: 30 base pairs
         (B) TYPE: nucleic acid
         (C) STRANDEDNESS: single
         (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:3:

TTCAAGGATC CTTGGGCCAA AAGCTATACC                                               30

(2) INFORMATION FOR SEQ ID NO:4:

(i) SEQUENCE CHARACTERISTICS:
         (A) LENGTH: 31 base pairs
         (B) TYPE: nucleic acid
         (C) STRANDEDNESS: single
         (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:4:

CATGGTAATC TAGATCCTCT GAAACCTCTG C                                                    31

(2) INFORMATION FOR SEQ ID NO:5:

(i) SEQUENCE CHARACTERISTICS:
        (A) LENGTH: 29 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:5:

GCGCTCTAGA TTGCCTCTGC AAAAGTTCC                                                       29

(2) INFORMATION FOR SEQ ID NO:6:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:6:

CAGAGTAAAA AAGGGAAGCT TACGAAAAAA ATTTCGTAAG G                                         41

(2) INFORMATION FOR SEQ ID NO:7:

(i) SEQUENCE CHARACTERISTICS:
        (A) LENGTH: 36 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:7:

CTTCCTTAAA TCAACAAGCT TTAAGAATAT ATTTCC                                               36

(2) INFORMATION FOR SEQ ID NO:8:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:8:

GCGCTCGAGG ATTTTCGTGC AAACAAGC                                                        28

(2) INFORMATION FOR SEQ ID NO:9:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:9:

ATTCTCTCGA GCAATGTCTG CTCTTTCG                    28

(2) INFORMATION FOR SEQ ID NO:10:

(i) SEQUENCE CHARACTERISTICS:
        (A) LENGTH: 28 base pairs
        (B) TYPE: nucleic acid
        (C) STRANDEDNESS: single
        (D) TOPOLOGY: linear (ii) MOLECULE TYPE: other nucleic acid (iii) HYPOTHETICAL: NO (iv) ANTI-SENSE: NO (xi) SEQUENCE DESCRIPTION: SEQ ID NO:10:

ACACAAGGAT CCACATCATT CCAATACC                    28